(12) United States Patent
Raulerson et al.

(10) Patent No.: US 7,914,518 B2
(45) Date of Patent: Mar. 29, 2011

(54) METHODS OF IMPLANTING A DUAL CATHETER

(75) Inventors: J. Daniel Raulerson, Brewton, AL (US); John Stephens, Perkiomenville, PA (US)

(73) Assignee: Medical Components, Inc., Harleysville, PA (US)

( * ) Notice: Subject to any disclaimer, the term of this patent is extended or adjusted under 35 U.S.C. 154(b) by 8 days.

(21) Appl. No.: 11/646,019

(22) Filed: Dec. 27, 2006

(65) Prior Publication Data

US 2007/0225683 A1    Sep. 27, 2007

Related U.S. Application Data

(62) Division of application No. 10/775,988, filed on Feb. 9, 2004.

(60) Provisional application No. 60/447,150, filed on Feb. 13, 2003.

(51) Int. Cl.
*A61M 5/00* (2006.01)
*A61M 39/00* (2006.01)
*A61M 31/00* (2006.01)

(52) U.S. Cl. .................. 604/533; 604/500; 604/250

(58) Field of Classification Search .................. 604/500, 604/534, 101.05; 251/6
See application file for complete search history.

(56) References Cited

U.S. PATENT DOCUMENTS

| | | | |
|---|---|---|---|
| 3,061,263 A | 10/1962 | Butler | |
| 3,461,876 A * | 8/1969 | Miller, Jr. | 606/120 |
| 3,571,861 A * | 3/1971 | Olson | 24/30.5 R |
| 3,576,054 A | 4/1971 | Rynk | |
| 4,192,304 A * | 3/1980 | Millet | 604/250 |
| 4,364,383 A * | 12/1982 | Vcelka | 604/407 |
| 4,382,453 A | 5/1983 | Bujan et al. | |
| 4,434,963 A * | 3/1984 | Russell | 251/7 |
| 4,475,709 A * | 10/1984 | Becker, Jr. | 251/6 |
| 4,514,882 A * | 5/1985 | Lavielle | 24/16 PB |
| 4,534,089 A * | 8/1985 | Swan | 24/559 |
| 4,923,153 A | 5/1990 | Matsui et al. | |
| 4,983,172 A | 1/1991 | Steer et al. | |
| 5,226,892 A * | 7/1993 | Boswell | 604/180 |
| 5,308,337 A | 5/1994 | Bingisser | |
| 5,395,343 A | 3/1995 | Iscovich | |
| 5,611,778 A | 3/1997 | Brinon | |
| 6,045,531 A * | 4/2000 | Davis | 604/101.05 |
| 6,058,572 A | 5/2000 | Folkmar | |
| 6,089,527 A | 7/2000 | Utterberg | |
| 6,228,064 B1 | 5/2001 | Abita et al. | |
| 6,247,211 B1 | 6/2001 | Bell | |
| 6,331,165 B1 * | 12/2001 | Turturro et al. | 600/562 |
| 6,453,185 B1 * | 9/2002 | O'Keefe | 600/378 |
| 6,460,231 B2 * | 10/2002 | Bourgerie | 24/487 |
| 6,638,242 B2 * | 10/2003 | Wilson et al. | 604/43 |
| 6,969,381 B2 * | 11/2005 | Voorhees | 604/534 |
| 2002/0087108 A1 * | 7/2002 | Maginot et al. | 604/5.04 |

* cited by examiner

*Primary Examiner* — Kevin C Sirmons
*Assistant Examiner* — Imani Hayman
(74) *Attorney, Agent, or Firm* — Anton P. Ness, Esq.; Fox Rothschild LLP

(57) ABSTRACT

A clamp (110) for releasably clamping a catheter, including a body having a first portion (112), a second portion (122), and a hinge (132) connecting the first portion and the second portion, such that the first portion is disposed to face the second portion. The first portion (112) includes a tab (134) extending distal from the hinge (132) and wherein the second portion (122) includes a locking means (146) for releasably locking the tab (134) to the second portion (122). A method of releasably clamping a plurality of catheter lumens (100,102) during catheter insertion and a method of locating a catheter insertion distance based on the location of the clamp are also disclosed.

8 Claims, 6 Drawing Sheets

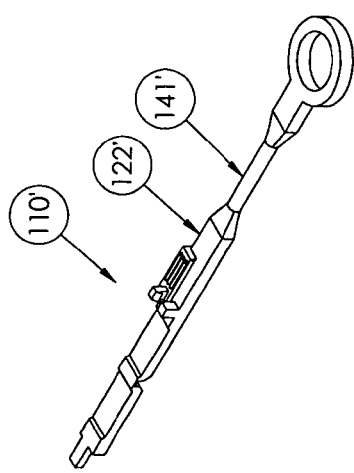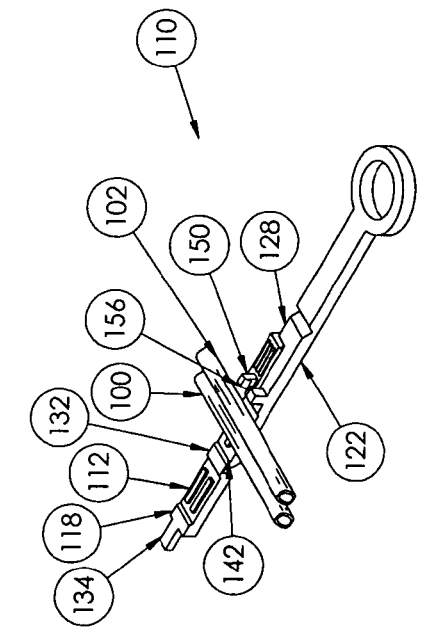

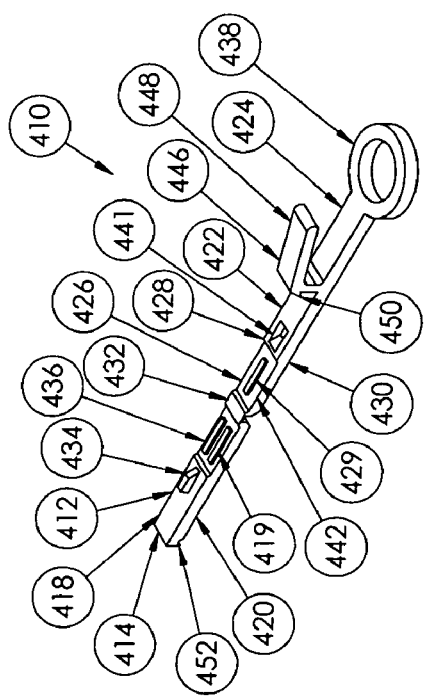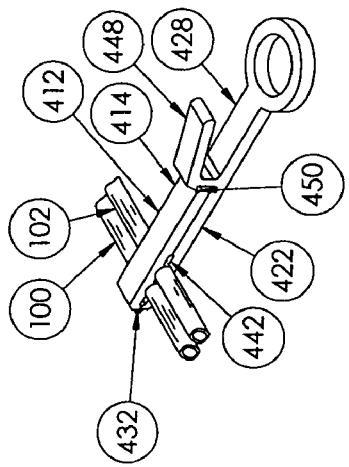
FIG. 9
FIG. 10

METHODS OF IMPLANTING A DUAL CATHETER

CROSS REFERENCE TO RELATED APPLICATIONS

The present application is a Divisional Application of U.S. patent application Ser. No. 10/775,988 filed Feb. 9, 2004, which claims the benefit of U.S. Provisional Patent Application Ser. No. 60/447,150, filed Feb. 13, 2003.

FIELD OF THE INVENTION

The present invention relates to a clamp for positioning a catheter in place during insertion into a patient.

BACKGROUND OF THE INVENTION

Catheters for the introduction or removal of fluids may be located in various venous locations and cavities throughout the body of a patient for the introduction of fluids to the body or removal of fluids from the body. Such catheterization may be performed by using a single catheter assembly having multiple lumens. A typical example of a multiple lumen catheter assembly is a dual lumen catheter assembly in which one lumen introduces fluids and one lumen removes fluids. Catheterization may also be performed by using separate, single lumen catheters inserted into an area to be catheterized. Examples of such multiple catheter assemblies are TESIO® catheters sold by Medical Components, Inc. of Harleysville, Pa.

Generally, to insert any catheter in a blood vessel, the vessel is identified by aspiration with a long hollow needle in accordance with the Seldinger technique. When blood enters a syringe attached to the needle, indicating that the vessel has been found, a thin guidewire is then introduced, typically through a syringe needle or other introducer device, into the interior of the vessel. The introducer device is then removed, leaving the end portion of the guidewire that has been inserted into the vessel within the vessel and the opposing end of the guidewire projecting beyond the surface of the skin of the patient.

At this point, several options are available to a physician for catheter placement. The simplest is to pass a catheter assembly into the vessel directly over the guidewire. The guidewire is then removed, leaving the catheter assembly in position within the vessel. However, this technique is only possible in cases where the catheter assembly is of a relatively small diameter, made of a stiff material and not significantly larger than the guidewire. For example, this technique may be used to insert small diameter dual lumen catheters into a patient. If the catheter assembly to be inserted is significantly larger than the guidewire, a dilator device is first passed over the guidewire to enlarge the hole. The dilator is then removed, and the catheter assembly is then passed over the guidewire into the vessel. The guidewire is then removed.

In the case of an individual, singe-lumen catheter typically used in multiple catheter assemblies (e.g., a TESIO® catheter assembly), a physician may use an introducer sheath. If a TESIO® catheter assembly is used for hemodialysis, for example, each catheter is inserted in two separate veins, such as femoral veins. Alternatively, each catheter may be inserted in two different locations of the same vein, such as the internal jugular vein. The introducer sheath is simply a large, stiff thin-walled tube which serves as a temporary conduit for the permanent catheter which is being placed. The introducer sheath is positioned by placing a dilator device inside of the introducer sheath and passing both the dilator and the introducer sheath together into the vessel over a guidewire. The guidewire, left in the vessel after its insertion as described above, and the dilator are then removed, leaving the thin-walled introducer sheath in place. The catheter is placed into the vessel through the introducer sheath. After the catheter is inserted into the vessel, the sheath is then torn from around the catheter and removed. Preferably, the catheter is inserted into the patient's vessel a predetermined distance, depending on the size of the patient and the physician's preference.

Typically, one catheter in the assembly, the venous catheter, is inserted farther into the patient than the other catheter in the assembly, the arterial catheter, to provide better blood circulation through the catheter assembly. Each of the catheters in the assembly is typically subcutaneously secured within the patient's body by a cuff located in a subcutaneous tunnel, or by otherwise externally affixing the catheter to the body.

The TESIO® catheter assembly may also be inserted in accordance with the technique described in U.S. Pat. No. 5,624,413 through a single insertion point using a sheath into the vessel. The TESIO® catheter assembly, once inserted in the vessel, is then tunnelled separately through the patient in two subcutaneous tunnels leading to outside the body of the patient, where the external, proximal portions of the catheter preferably are secured. After tunneling, clamps and luer locks are secured to the proximal end of each catheter in the assembly for connection to an external device, such as a hemodialysis machine.

One problem experienced by physicians while inserting the TESIO® catheter assembly occurs after the catheter assembly is inserted into the vessel, is that occasionally, while subcutaneously tunneling the catheter assembly through the body of the patient, the distal end of one or both catheters in the assembly may be pulled away from the predetermined location in which the physician initially inserted the catheter. Such a situation could reduce the effectiveness of the hemodialysis process. It would be beneficial to provide a mechanism by which the individual catheters in the catheter assembly are secured relative to each other, and in which the physician can determine whether the placement of the catheters in the vessel has changed after the catheter is inserted into the vessel.

BRIEF SUMMARY OF THE INVENTION

Briefly, the present invention provides a clamp comprising a body having a first portion, a second portion, and a hinge connecting the first portion and the second portion, such that the first portion is disposable to face against the second portion when clamping around and to either one catheter lumen or a side-by-side pair of catheter lumens proximate to the hinge. The first portion includes a tab extending distal from the hinge and wherein the second portion includes a locking means for releasably locking the tab to the second portion.

Additionally, the present invention provides a method of releasably clamping a catheter assembly. The method comprises inserting a distal end of a first catheter lumen into a patient at an insertion site; inserting a distal end of a second catheter lumen into the patient to a location proximal to that of the distal end of the first catheter lumen; releasably clamping the first and second catheter lumens proximate to the insertion site; but distal of the proximal ends thereof; subcutaneously tunneling a proximal end of each of the first and second catheter lumens; installing catheter locking devices on the proximal ends of each of the first and second catheter lumens; and later releasing the catheter clamp when desired.

Further, the present invention provides a method of relocating a catheter insertion distance in a patient. The method comprises inserting a distal end of a first catheter lumen into a patient; inserting a distal end of a second catheter lumen into the patient to a location proximal to that of the distal end of the first catheter lumen; releasably clamping the first and second catheter lumens at a predetermined location with a catheter clamp; distal of the proximal ends thereof; subcutaneously tunneling a proximal end of each of the first and second catheter lumens; determining whether the distal ends of the first and second catheter lumens have been dislodged by comparing the location of the catheter clamp to the predetermined location; moving the catheter clamp to the predetermined position; and later releasing the catheter clamp when desired.

BRIEF DESCRIPTION OF THE DRAWINGS

The accompanying drawings, which are incorporated herein and constitute part of this specification, illustrate the presently preferred embodiments of the invention, and, together with the general description given above and the detailed description given below, serve to explain the features of the invention. In the drawings:

FIG. 1A is a perspective view of a second embodiment of a catheter clamp.

FIG. 3 is a perspective view of the catheter clamp of FIG. 1, with a pair of catheter lumens, in an open position.

FIG. 9 is a perspective view of a catheter clamp according to a fifth embodiment of the present invention.

FIG. 10 is a perspective view of the catheter clamp of FIG. 9, with a pair of catheter lumens, in a closed position.

DETAILED DESCRIPTION OF THE INVENTION

Figure 1:
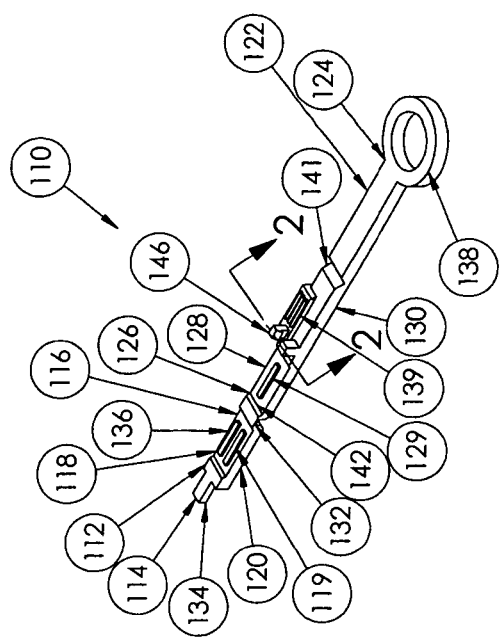
FIG. 1 is a perspective view of a catheter clamp according to a first embodiment of the present invention.

In the drawings, like numerals indicate like elements throughout. Certain terminology is used herein for convenience only and is not to be taken as a limitation on the present invention. The terminology includes the words above specifically mentioned, derivatives thereof, and words of similar import. The following describes preferred embodiments of the invention. However, it should be understood based on this disclosure, that the invention is not limited by the preferred embodiments described herein.

Figure 2:
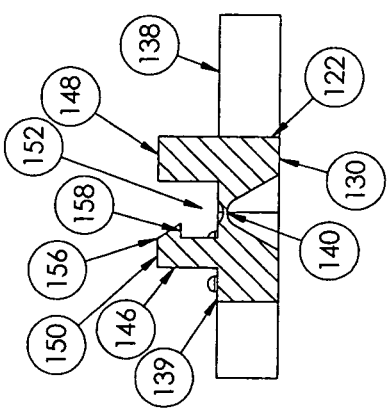
FIG. 2 is an enlarged sectional view of the catheter clamp taken along lines 2-2 of FIG. 1.

Referring to FIGS. 1 and 2, a catheter clamp 110 according to a first embodiment of the present invention is shown. While the clamp 110 is preferably used to clamp a catheter, those skilled in the art will recognize that the clamp 110 may be used to clamp other catheters. The clamp 110 is preferably a unitary construction made from a polymer, such as, for example polypropylene, although those skilled in the art will recognize that other suitable materials may be used. The clamp 110 may be fabricated by injection molding or other known process.

The clamp 110 is preferably a generally elongated strip comprised of a first portion 112 having a free end 114 and a connected end 116. A top face 118 extends between the free end 114 and the connected end 116. Optionally, the top face 118 may include at least one longitudinal rib 119 extending outwardly therefrom, or two such ribs as shown. A bottom face 120, disposed away from the top face 118, also extends between the free end 114 and the connected end 116. The clamp 110 is further comprised of a second portion 122 having a free end 124 and a connected end 126. A top face 128 extends between the free end 124 and the connected end 126. Optionally, the top face 128 may include at least one longitudinal rib 129 extending outwardly therefrom. Preferably, the at least one longitudinal rib 129 is offset from the at least one longitudinal rib 119 on the first portion 112. A bottom face 130, disposed away from the top face 128, also extends between the free end 124 and the connected end 126. The second portion 122 also preferably includes a gripping ring 138 disposed at the free end 124. The gripping ring 138 facilitates gripping the clamp 110 by the inserting physician during catheter insertion.

A hinge 132, preferably a living hinge, connects the connected end 116 of the first portion 112 to the connected end 126 of the second portion 122. The hinge 132 is disposed to allow the first portion 112 to rotate about the hinge 132 so that the top face 118 of the first portion 112 is able to engage the top face 128 of the second portion 122.

The free end 114 of the first portion 112 includes a free end portion or narrow elongate tab 134 that extends away from the hinge 132. The first portion 112 also includes a recessed portion 136 disposed on the top face 118 proximate to the connected end 116. The second portion 122 includes a recessed portion 142 disposed on the top face 128 proximate to the connected end 126.

The top face 128 of the second portion 122 also includes a lock 146 that secures the tab 134 when the first portion 112 is pivoted about the hinge 132 so that the top face 118 of the first portion 112 engages the top face 128 of the second portion 122. FIG. 2 shows a sectional view of the lock 146. The lock 146 is comprised of a guide 148 that extends generally orthogonally from the top face 128 of the second portion 122 and a cantilevered portion 150 that also extends generally orthogonally from the top face 128 of the second portion 122, with a longitudinal channel 152 separating the guide 148 and the cantilevered portion 150. The cantilevered portion 150 is disposed on a ledge 139 that extends away from the second portion 122. The ledge 139 is connected to the second portion 122 by a recessed portion 140. The recessed portion 140 is a flexible section that allows the ledge to be biased about the recessed portion 140 to permit pivoting of the cantilevered portion 150 away from the guide 148, thus allowing the tab 134 to be disposed within the channel 152 to releasably lock the free end 114 of the first portion to the second portion 122.

The cantilevered portion 150 includes a beveled face 156 that guides the tab 134 toward the guide 148 and into the channel 152. The cantilevered portion 150 also includes a latching ledge 158 that extends partially over and partially into the channel 52. The latching ledge 158 extends toward the guide 148 and into the channel 152 sufficiently so that the channel 152 is narrower than the tab 134 at the latching ledge 158.

The second portion 122 also preferably includes a weakened portion 141 disposed between the free end 124 and the lock 146. The weakened portion 141, shown in FIG. 1 as a generally transverse "V-shaped" cutout or groove, allows the free end 124 to flex relative to the remaining part of the second portion 122 to provide the inserting physician with some flexibility in gripping and maneuvering the clamp 110.

An alternate embodiment of a clamp 110', shown in FIG. 1A, shows a clamp similar to the clamp 110, but with a weakened portion 141' as a narrowed part of the second portion 122' to provide the desired flexibility. Other features of the clamp 110' are preferably the same or similar to corresponding features in the clamp 110.

Figure 4:
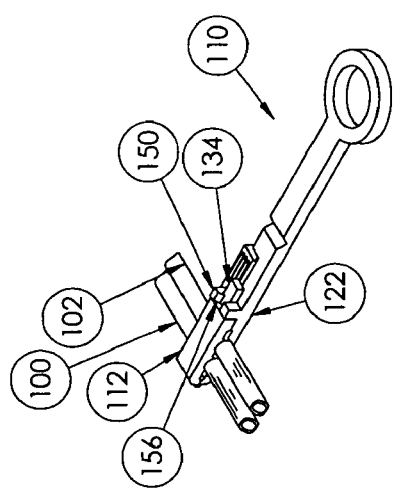
FIG. 4 is a perspective view of the catheter clamp of FIG. 1, with a pair of catheter lumens, in a closed position.

Operation of the clamp 110 is illustrated in FIGS. 3 and 4, with reference to the sectional view of FIG. 2. Operation of the clamp 110' is identical to operation of the clamp 110 and needs not be discussed. At least one, and preferably two catheters 100, 102 are disposed within the recessed portion 142. The first portion 112 is pivoted about the hinge 132 toward the second portion 122 so that the top face 118 of the first portion 112 faces the top face 128 of the second portion 122 and traversing the catheter lumens 100,102. The tab 134 engages the beveled face 156 of the cantilevered portion 150, wherein the tab 134 is guided into the channel 152. Since the channel 152 is narrower than the tab 134 at the latching ledge 158, the cantilevered portion 150 bends about the recessed portion 140 away from the channel 152, the recessed portion defining a flexible section. As the tab 134 clears the latching ledge 158, the cantilevered portion 150 snaps back to its original position, locking the tab 134 in the channel 152 between the latching ledge 158 and the top face 128 of the second portion 122 and latches atop a side edge of tab 134.

The ribs 119, 129 engage the catheters 100, 102 to securely retain the catheters 100, 102 within the clamp 110 and secured against longitudinal movement relative to each other. Optionally, the ribs 119, 129 may compress the catheters 100, 102 sufficiently to occlude the catheters 100, 102, preventing blood loss from the patient through the catheters 100, 102, or preventing an air embolism from being aspirated into the patient through the catheter 100, 102. However, those skilled in the art will recognize that, even if the ribs 119, 129 are omitted, the clamp 110, when in the closed position, may sufficiently prevent blood loss and/or air embolism.

Figure 5:
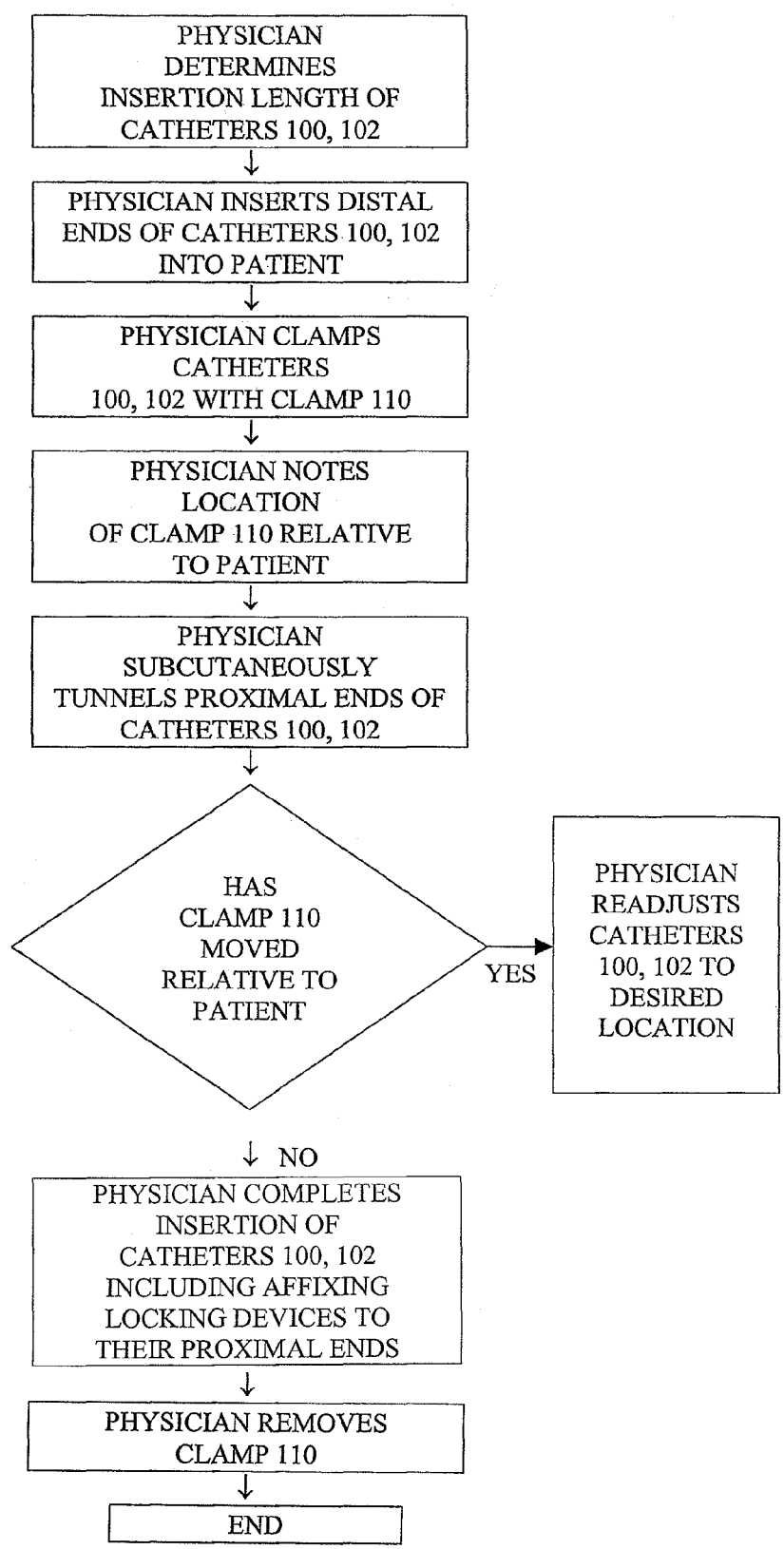
FIG. 5 is a flow chart showing the steps to ensure that desired catheter placement location is maintained during catheter tunneling.

The clamp 110 provides the ability for the implanting physician to ensure that the catheters 100, 102 are not dislodged from the patient's blood vessel during tunneling. Referring to the flow chart of FIG. 5, prior to insertion of the catheters 100, 102, the physician determines how far into the patient's blood vessel that the catheters 100, 102 are to be inserted in order to optimize blood circulation through the catheters 100, 102. Occasionally, during the tunneling procedure, the catheters 100, 102 may be inadvertently pulled from their desired location, reducing the efficiency of the catheters 100, 102.

To minimize such problem, after the catheters 100, 102 are inserted into the patient, but before the proximal ends of the catheters 100, 102 are subcutaneously tunneled, the clamp 110 may be repositioned along the length of the catheters 100, 102, such as where the catheters 100, 102 enter the patient's skin. After the physician forms the tunnel and pulls the proximal ends of the catheters 100, 102 through the tunnel, the physician needs merely to see if the clamp 110 is still positioned at the entrance of the catheters 100, 102 into the patient. If the clamp 110 has been moved away from that location, the physician knows that the catheters 100, 102 have been longitudinally translated during tunneling, and that the catheters 100, 102 must be readjusted in the blood vessel. While holding the catheters 100, 102, the physician moves the clamp 110 back against the entrance of the catheters 100, 102 into the patient's skin. The physician may remove the clamp 110 from the catheters 100, 102 after the proximal ends of the catheters 100, 102 are otherwise clamped off. To remove the clamp 110, the ledge 139 is depressed so that the ledge 139 pivots about the recessed portion 140. The cantilevered portion 150 is disposed away from the guide 148, allowing the first portion 112 to pivot about the hinge 132, and allowing the tab 134 to be removed from the channel 152, releasing the first and second catheters 100, 102 from the clamp 110.

Figure 6:
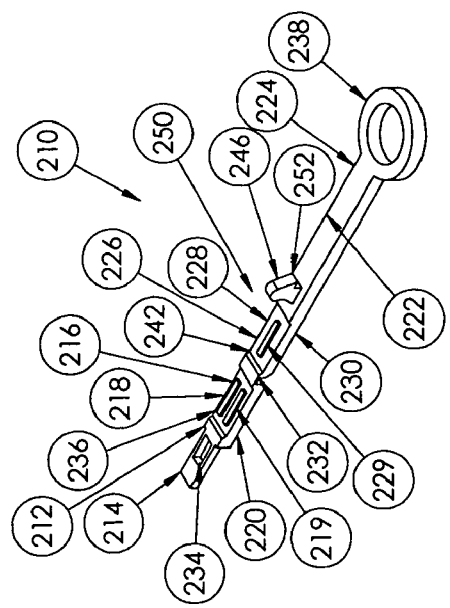
FIG. 6 is a perspective view of a catheter clamp according to a third embodiment of the present invention.
Figure 7:
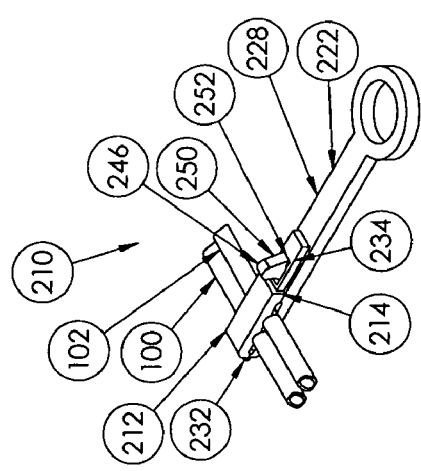
FIG. 7 is a perspective view of the catheter clamp of FIG. 6, with a pair of catheter lumens, in a closed position.

An alternative embodiment of the present invention is a catheter clamp 210 as shown in FIGS. 6 and 7. The clamp 210 is comprised of a first portion 212 having a free end 214 and a connected end 216. A top face 218 extends between the free end 214 and the connected end 216. The top face 218 includes a recessed portion 236. Optionally, the top face 218 may include at least one longitudinal rib 219 extending outwardly therefrom. An outside face 220, disposed away from the top face 218, also extends between the free end 214 and the connected end 216. The clamp 210 is further comprised of a second portion 222 having a free end 224 and a connected end 226. A top face 228 extends between the free end 224 and the connected end 226. The top face 228 includes a recessed portion 242. Optionally, the top face 228 may include at least one longitudinal rib 229 extending outwardly therefrom. Preferably, the at least one longitudinal rib 229 is offset from the at least one longitudinal rib 219 on the first portion 212. An outside face 230, disposed away from the top face 228, also extends between the free end 224 and the connected end 226. The second portion 222 also preferably includes a gripping ring 238 disposed at the free end 224. The gripping ring 238 facilitates gripping the clamp 210 by the inserting physician during catheter insertion.

A hinge 232, preferably a living hinge, connects the connected end 216 of the first portion 212 to the connected end 226 of the second portion 222. The hinge 232 is disposed to allow the first portion 212 to rotate about the hinge 232 so that the top face 218 of the first portion 212 is able to generally face the top face 228 of the second portion 222.

The first portion 212 includes a free end portion having a slot 234 that extends longitudinally between the free end 214 and the connecting end 216. The second portion 222 also includes a vertically projecting tab or lock 246 that engages the slot 234 when the first portion 212 is pivoted about the hinge 232 so that the top face 218 of the first portion 212 faces the top face 228 of the second portion 222. The lock 246 is comprised of a locking member 250 having a rounded top and that extends generally obliquely from the top face 228 of the second portion 222. A cantilevered portion 252 extends away from the locking member 250 toward the free end 224 of the second portion 222 and includes a ledge that latches atop an edge of slot 234. Between the ledge and the rounded top the surface of the cantilevered portion is shown to be beveled.

In operation, catheters 100, 102 are disposed on the top face 228 of the second portion 222, within the recessed portion 242, as shown in FIG. 7. The first portion 212 is pivoted about the hinge 232 so that the slot 234 is disposed toward the lock 246. The oblique disposition of the locking member 250 with respect to the second portion 222 biases the locking member 250 toward the hinge 232, allowing the tab 234 to pass under the cantilevered portion 252. After the slot 234 clears the cantilevered portion 252, the biasing member 250 returns to its prebiased position, and the free end 214 of the first portion 212 is locked under the cantilevered portion 252, as seen in FIG. 7.

The ribs 219, 229 engage the catheters 100, 102 to securely retain the catheters 100, 102 within the clamp 210. Optionally, the ribs 219, 229 may compress the catheters 100, 102 sufficiently to occlude the catheters 100, 102, preventing blood loss from the patient through the catheters 100, 102, or preventing an air embolism from being aspirated into the patient through the catheter 100, 102. However, those skilled in the art will recognize that, even if the ribs 219, 229 are omitted, the clamp 210, when in the closed position, may sufficiently prevent blood loss and/or air embolism.

To unlock the clamp 210, the user places a thumb or finger on the top of the cantilevered portion 252 and biases the locking member 250 toward the hinge 232. The cantilevered portion 252 clears the free end 214 of the first portion 212, allowing the first portion 212 to pivot about the hinge 232, opening the clamp 210 and releasing the catheters 100, 102. The clamp 210 may also be used to practice the method of relocating a catheter insertion distance in a patient illustrated above with clamp 110.

Figure 8:
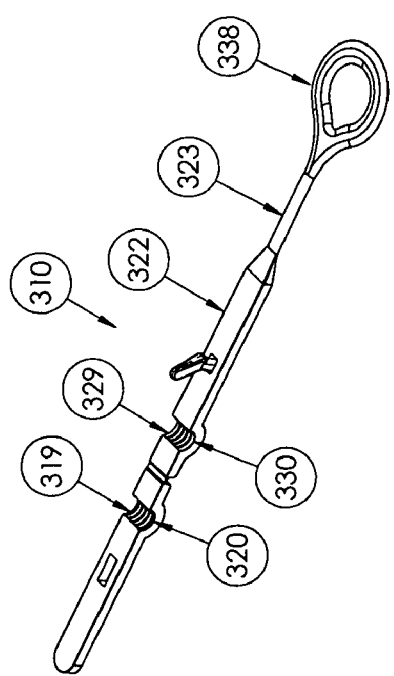
FIG. 8 is a perspective view of a catheter clamp according to a fourth embodiment of the present invention.

An alternate embodiment of a clamp 310 is shown in FIG. 8. The clamp 310 is similar to the clamp 210, with the exception that the clamp 310 includes generally rounded recessed portions 319, 329 instead of the generally flat recessed portions 236, 242 shown in the clamp 210 of FIG. 6. Each generally rounded recessed portion 319, 329 may include at least one longitudinally extending rib 320, 330, respectively. Additionally, the clamp 310 includes a narrowed neck 323 of the second portion 322 which allows for flexibility of the clamp 310 relative to the gripping ring 338 to facilitate use by the inserting physician. Operation of the clamp 310 is preferably similar to the operation of the clamp 210 as described above.

Another embodiment of a clamp 410 is shown in FIG. 9. The clamp 410 is preferably a generally elongated strip comprised of a first portion 412 having a free end portion 414 concluding in a free end edge, and a connected end 416. A top face 418 extends between the free end 414 and the connected end 416. Optionally, the top face 418 may include at least one longitudinal rib 419 extending outwardly therefrom. A bottom face 420, disposed away from the top face 418, also extends between the free end 414 and the connected end 416. The clamp 410 is further comprised of a second portion 422 having a free end 424 and a connected end 426. A top face 428 extends between the free end 424 and the connected end 426. Optionally, the top face 428 may include at least one longitudinal rib 429 extending outwardly therefrom. Preferably, the at least one longitudinal rib 429 is offset from the at least one longitudinal rib 419 on the first portion 412. A bottom face 430, disposed away from the top face 428, also extends between the free end 424 and the connected end 426. The second portion 422 also preferably includes a gripping ring 438 disposed at the free end 424. The gripping ring 438 facilitates gripping the clamp 410 by the inserting physician during catheter insertion.

A hinge 432, preferably a living hinge, connects the connected end 416 of the first portion 412 to the connected end 426 of the second portion 422. The hinge 432 is disposed to allow the first portion 412 to rotate about the hinge 432 so that the top face 418 of the first portion 412 is able to engage the top face 428 of the second portion 422.

The free end 414 of the first portion 412 includes a vertical projection 434 that extends away from the top face 418. The first portion 412 also includes a recessed portion 436 disposed on the top face 418 proximate to the connected end 416. The second portion 422 includes slot 441 complementary to vertical projection 434 of first portion 412, and also a recessed portion 442 disposed on the top face 428 proximate to the connected end 426.

The top face 428 of the second portion 422 also includes a vertically projecting tab or lock 446 that secures the transverse end edge of free end 414 of the first portion 412 when the first portion 412 is pivoted about the hinge 432 so that the top face 418 of the first portion 412 engages the top face 428 of the second portion 422. The lock 446 includes a cantilevered portion 448 that extends away from the top face 438 and toward the free end 424 of the second portion 422. The lock 446 also includes a ledge 450 that extends toward the connected end 426 of the second portion 422, and locks atop a transverse end edge of free end 414. The free end 414 of the first portion 412 may optionally include a recess 452 along the bottom face 420 that is engageable with the tab 450 when the clamp 410 is in a closed position.

Operation of the clamp 410 is illustrated in FIG. 10. At least one, and preferably two catheters 100, 102 are disposed within the recessed portion 442. The first portion 412 is pivoted about the hinge 432 toward the second portion 422 so that the top face 418 of the first portion 412 faces the top face 428 of the second portion 422. The cantilevered portion 448 is biased toward the top face 428 of the second portion 422 and the free end 414 of the first portion is disposed under the tab 450. Generally simultaneously, the tab 434 engages the slot 441 to lock the top face 418 of the first portion 412 and the top face 438 of the second portion 422 together. The cantilevered portion 448 is released, securing the free end 414 of the first portion 412 under the tab 450.

The ribs 419, 429 engage the catheters 100, 102 to securely retain the catheters 100, 102 within the clamp 410. Optionally, the ribs 419, 429 may compress the catheters 100, 102 sufficiently to occlude the catheters 100, 102, preventing blood loss from the patient through the catheters 100, 102, or preventing an air embolism from being aspirated into the patient through the catheter 100, 102. However, those skilled in the art will recognize that, even if the ribs 419, 429 are omitted, the clamp 410, when in the closed position, may sufficiently prevent blood loss and/or air embolism.

To release the clamp 410, the cantilevered portion 448 is biased toward the top face 428 of the second portion 422, releasing the free end 414 of the first portion 412. The first portion 412 is pivoted about the hinge 432, releasing the catheters 100, 102 from the clamp 410. The clamp 410 may also be used to practice the method of relocating a catheter insertion distance in a patient illustrated above with clamp 110.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

What is claimed is:
1. A method of releasably clamping a catheter assembly comprising the steps of, in sequence:
   providing a catheter clamp;
   inserting a distal end of a first catheter into a patient at a vascular insertion site to a predetermined position in vasculature of the patient;
   releasably clamping the first catheter with the catheter clamp proximate to the vascular insertion site and at a location spaced distally from a proximal end of the first catheter;
   subcutaneously tunneling a proximal end portion of the first catheter proximal of the catheter clamp;
   installing a catheter locking device on the proximal end of the first catheter for clamping off the catheter; and
   releasing the catheter clamp subsequent to clamping off the proximal end thereof.

2. The method according to claim 1, further comprising the step of, prior to the tunneling step, inserting into the vascular insertion site a second catheter separate from and longitudinally movable with respect to the first catheter, to coextend therealong, to a predetermined position in the vasculature, and releasably clamping in common the first and second catheters proximate the vascular insertion site.

3. The method according to claim 1, further comprising, after installing the catheter locking device, verifying whether the clamp moved relative to the insertion site.

4. The method according to claim 3, further comprising, after verifying that the clamp had moved relative to the insertion site, readjusting the clamp to its previous position proximate to the insertion site, thereby moving the first catheter to its predetermined position in the vasculature.

5. The method according to claim 1, wherein releasably clamping the first catheter comprises occluding the first catheter.

6. A method of relocating a catheter insertion distance in a patient comprising the steps of:
providing a catheter clamp for clamping first and second side-by-side catheters in common;
inserting a distal end of a first catheter into a patient at a vascular insertion site to a predetermined position in vasculature of the patient;
separately inserting a distal end of a second catheter into the patient at the vascular insertion site to a location proximal to that of the distal end of the first catheter, to a predetermined position in the vasculature;
then releasably clamping the first and second catheters with the catheter clamp at a predetermined location spaced distally from the catheter proximal ends and proximate to the vascular insertion site;
then subcutaneously tunneling a proximal end of each of the first and second catheters subsequent to the step of releasably clamping;
then determining whether the distal ends of the first and second catheters have been dislodged by comparing the location of the catheter clamp to the predetermined location;
then moving the catheter clamp with the first and second catheters held therein to its predetermined location, thereby moving the first and second catheters to the predetermined position within the patient's vasculature; and
then releasing the catheter clamp.

7. The method according to claim 6, further comprising the step of, after tunneling and prior to releasing the catheter clamp, installing catheter locking devices on the proximal ends of each of the first and second catheters for clamping off the catheters.

8. The method according to claim 6, wherein releasably clamping the first and second catheters comprises occluding the first and second catheters.

* * * * *